(12) United States Patent
Brown et al.

(10) Patent No.: US 9,033,888 B2
(45) Date of Patent: May 19, 2015

(54) ULTRASOUND IMAGING SYSTEM USING BEAMFORMING TECHNIQUES FOR PHASE COHERENCE GRATING LOBE SUPPRESSION

(75) Inventors: Jeremy Brown, Halifax (CA); Robert Adamson, Halifax (CA); Zahra Torbatian, Halifax (CA); Manohar Bance, Halifax (CA)

(73) Assignee: DALHOUSIE UNIVERSITY, Halifax, NS (CA)

( * ) Notice: Subject to any disclaimer, the term of this patent is extended or adjusted under 35 U.S.C. 154(b) by 0 days.

(21) Appl. No.: 13/574,844

(22) PCT Filed: Feb. 8, 2011

(86) PCT No.: PCT/IB2011/000430
§ 371 (c)(1),
(2), (4) Date: Jul. 24, 2012

(87) PCT Pub. No.: WO2011/095896
PCT Pub. Date: Aug. 11, 2011

(65) Prior Publication Data
US 2012/0296215 A1    Nov. 22, 2012

Related U.S. Application Data

(60) Provisional application No. 61/302,242, filed on Feb. 8, 2010.

(51) Int. Cl.
*A61B 8/14* (2006.01)
*G01S 7/52* (2006.01)
(Continued)

(52) U.S. Cl.
CPC ........... *G01S 7/52047* (2013.01); *A61B 8/5269* (2013.01); *G01S 15/8927* (2013.01);
(Continued)

(58) Field of Classification Search
None
See application file for complete search history.

(56) References Cited

U.S. PATENT DOCUMENTS

| 3,877,031 A | 4/1975 | Mailloux et al. |
| 4,228,436 A | 10/1980 | DuFort |

(Continued)

FOREIGN PATENT DOCUMENTS

| EP | 0634138 A1 | 1/1995 |
| EP | 1477118 A1 | 11/2004 |

(Continued)

OTHER PUBLICATIONS

Camacho, J., et al., "Phase Coherence Imaging," IEEE Transactions on Ultrasonics, Ferroelectrics and Frequency Control, vol. 56, No. 5, pp. 958-974, May 2009.

(Continued)

*Primary Examiner* — Long V Le
*Assistant Examiner* — Kevin Pontius
(74) *Attorney, Agent, or Firm* — Lynn C. Schumacher; Stephen W. Leonard; Hill & Schumacher

(57) ABSTRACT

High-frequency ultrasound imaging can be performed with greater quality and suppressed grating lobes by using methods and systems for effectively reducing the temporal length of transmit grating lobe signals in received ultrasound echoes. Systems and methods are provided for improved high-frequency ultrasound imaging. In various aspects, the method of shortening the time domain of grating lobe signals comprises splitting an array of N transmit elements into K sub-apertures. In further aspects, the grating lobes are suppressed by performing signal processing of the shortened grating lobe signals. In certain aspects, the signal processing method comprises weighting the samples by a calculated phase coherence factor.

23 Claims, 15 Drawing Sheets

(51) Int. Cl.
*A61B 8/08* (2006.01)
*G01S 15/89* (2006.01)
*G10K 11/34* (2006.01)

(52) U.S. Cl.
CPC ......... *G01S15/8956* (2013.01); *G01S 15/8997* (2013.01); *G10K 11/346* (2013.01); *G01S 15/8915* (2013.01)

(56) References Cited

U.S. PATENT DOCUMENTS

| | | | |
|---|---|---|---|
| 4,318,104 A | 3/1982 | Enein | |
| 4,542,653 A | 9/1985 | Liu | |
| 5,322,068 A * | 6/1994 | Thiele et al. | 600/447 |
| 5,349,262 A | 9/1994 | Grenon et al. | |
| 6,689,063 B1 | 2/2004 | Jensen et al. | |
| 7,207,942 B2 | 4/2007 | Ustuner et al. | |
| 7,265,713 B2 | 9/2007 | Lewis | |
| 7,527,592 B2 | 5/2009 | Haugen et al. | |
| 7,534,209 B2 | 5/2009 | Abend et al. | |
| 7,701,380 B2 | 4/2010 | Altes | |
| 7,887,486 B2 | 2/2011 | Ustuner et al. | |
| 7,972,271 B2 | 7/2011 | Johnson et al. | |
| 8,057,393 B2 | 11/2011 | Yao et al. | |
| 2004/0267127 A1 | 12/2004 | Abend et al. | |
| 2005/0033165 A1 | 2/2005 | Ustuner et al. | |
| 2005/0131298 A1* | 6/2005 | Cai | 600/447 |
| 2005/0228279 A1* | 10/2005 | Ustuner et al. | 600/443 |
| 2005/0288588 A1* | 12/2005 | Weber et al. | 600/447 |
| 2007/0173722 A1 | 7/2007 | Ustuner et al. | |
| 2007/0242567 A1* | 10/2007 | Daft et al. | 367/140 |
| 2008/0125660 A1* | 5/2008 | Yao et al. | 600/459 |
| 2009/0005684 A1* | 1/2009 | Kristoffersen et al. | 600/447 |
| 2009/0066727 A1* | 3/2009 | Lu et al. | 345/643 |
| 2009/0141957 A1 | 6/2009 | Yen et al. | |
| 2010/0174194 A1 | 7/2010 | Chiang et al. | |
| 2010/0194629 A1 | 8/2010 | Craig et al. | |
| 2010/0249596 A1 | 9/2010 | Magee | |
| 2011/0319764 A1 | 12/2011 | Okada et al. | |
| 2012/0029357 A1 | 2/2012 | Chiang et al. | |

FOREIGN PATENT DOCUMENTS

| | | |
|---|---|---|
| ES | 2 332 637 A1 | 2/2010 |
| JP | 5-277117 | 10/1993 |
| JP | 10-127633 | 5/1998 |
| JP | 2003-235839 | 8/2003 |
| JP | 2009-535097 | 10/2009 |
| JP | 2011-101721 | 5/2011 |
| WO | 2007/127147 A2 | 11/2007 |
| WO | WO 2010/018282 A1 | 2/2010 |
| WO | WO 2012/078610 A2 | 6/2012 |
| WO | WO 2012/091280 A1 | 7/2012 |

OTHER PUBLICATIONS

Gavrilov, L.R., et al., "A method of reducing grating lobes associated with an ultrasound linear phased array intended for transcrectal thermotherapy," IEEE Transactions on Ultrasonics, Ferroelectrics and Frequency Control, vol. 44, No. 5, pp. 1010-1017, Sep. 1997.

Li, P.C., et al., "Adaptive imaging using the generalized coherence factor," IEEE Transactions on Ultrasonics, Ferroelectrics and Frequency Control, vol. 50, No. 2, pp. 128-141, Feb. 2003.

Patent Cooperation Treaty, International Search Report and Written Opinion, International Patent Application No. PCT/IB2011/000430, Jul. 19, 2011, 7 Pages.

Rew, C.Y., et al., "Elimination of all grating lobes in ultrasonic synthetic focusing using a linear array," Electronics Letter, vol. 29, No. 19, pp. 1729-1731, Sep. 17, 1993.

Wang, H., et al., "Grating lobe reduction in a phased array of limited scanning," IEEE Trans. Antennas and Propagation, vol. 56, No. 6, pp. 1581-1586, Jun. 2008.

* cited by examiner

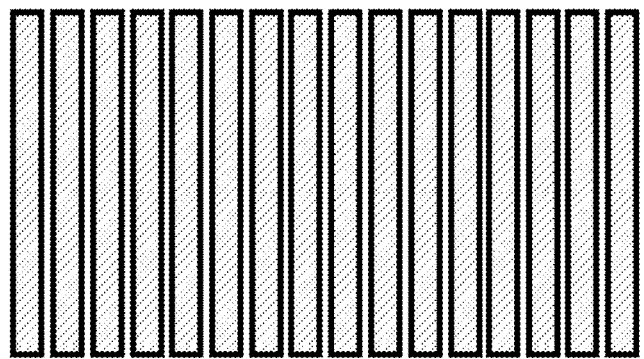
Figure 1A – Prior Art
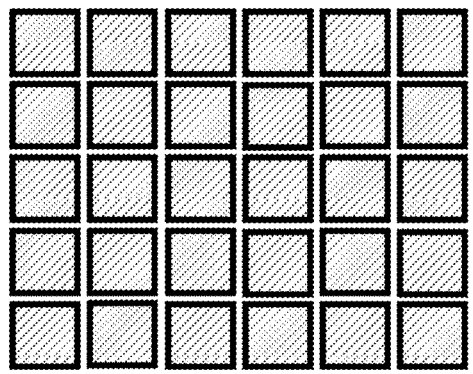
Figure 1B – Prior Art
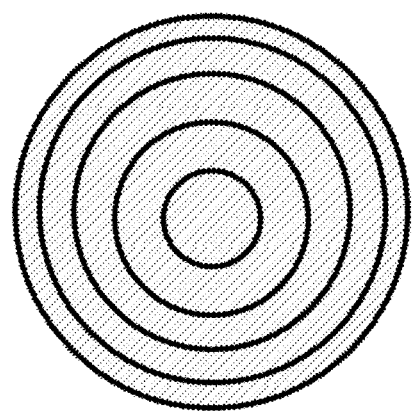
Figure 1C – Prior Art

ULTRASOUND IMAGING SYSTEM USING BEAMFORMING TECHNIQUES FOR PHASE COHERENCE GRATING LOBE SUPPRESSION

CROSS REFERENCE TO RELATED APPLICATIONS

This application claims the benefit of U.S. Provisional Application No. 61/302,242, filed Feb. 8, 2010, the entire disclosure of which is hereby incorporated by reference in its entirety for all purposes.

FIELD OF THE DISCLOSURE

This invention relates generally to ultrasound imaging systems, and more particularly to suppressing grating lobes in an ultrasound imaging system.

BACKGROUND

Low-frequency ultrasound imaging systems are very commonly used in diagnostic medicine, and they have been used for over 50 years. New high-frequency ultrasound imaging technology offers dramatic improvements in image resolution compared to these conventional low-frequency systems. Notwithstanding the increased performance that is possible with high-frequency ultrasound imaging, there are many technical barriers preventing its widespread use. Some of these barriers may be addressed by using array-based systems for high-frequency ultrasound imaging, but fabricating transducer arrays and the associated beamformers is more difficult for high-frequency systems since much smaller dimensions are involved (e.g., the element to element pitch of the transducer).

If an array is fabricated without having sufficiently small dimensions, large image artifacts result called grating lobes. Another unsolved problem of existing systems is that there is no simple and effective way to suppress grating lobes for ultrasound imaging systems that have array transducers with a large element-to-element pitch. One technique that has been proposed for suppressing the grating lobes is described in J. Camacho, M. Parrilla, and C. Fritsch, "Phase Coherence Imaging," *IEEE Trans. Ultrason., Ferroelectr., Freq. Control*, Vol. 56, No. 5, pp. 958-974, 2009. This technique, called "phased coherence imaging," suppresses grating lobes using phase coherence correction factor receive beamforming and synthetic aperture transmit beamforming.

Synthetic aperture beamforming is not suitable for use in high-frequency ultrasound imaging where small vibrations can create phase shifts in the received signals. Although synthetic aperture beamforming can produce high frame rates for generating full 2D images, all of the elements need to be pulsed individually before the beamforming delays are inserted. This means that this beamforming technique is susceptible to image distortion due to the large amount of time expired during the acquisition of the pre-beamformed signals. This image distortion is avoided however when implementing transmit focal-zone beamforming. Although only one A-scan line can be collected per transmit event, image distortion due to small motion artifacts is avoided due to the small amount of time expired between beamforming events. Unfortunately, for phase coherence imaging, transmit beamforming creates very long pulses in the grating lobe region which, upon returning to the array elements, create very long narrow band receive pulses. Consequently, when phase coherence correction factors are calculated from the received echoes in the same temporal region as the main lobe, there are no longer any random phases present since all of the long grating lobe echoes now overlap and for a certain time duration, are virtually all in-phase.

Thus, a need exists in the art for improved methods that effectively shorten the grating lobe signals in received ultrasound echoes, thereby enabling improved signal processing and suppression of grating lobes.

SUMMARY

The present disclosure addresses long-felt needs in the field of ultrasound imaging by providing systems and methods for effectively reducing the temporal length of transmit grating lobe signals in received ultrasound echoes. By shortening the grating lobe signals, the grating lobes can subsequently be suppressed using signal processing, e.g., by application of a calculated phase coherence factor. In this way, the present methods advantageously make possible the performance of high-frequency ultrasound imaging with improved image resolution.

Various aspects of the present disclosure provide techniques for transmit beamforming to be used with a phase coherence imaging technique that allow this technique to be used to suppress grating lobes in a practical, real ultrasound imaging system. The phase coherence imaging technique is enabled by using a transmit beamforming approach that effectively shortens the time-domain signal of the received echoes. In some aspects, the phase coherence imaging comprises sign coherence factor (SCF) weighting. By producing shorter time-domain signals, the present methods create a situation in which a smaller number of the received echoes overlap upon being received by the imaging transducer making the SCF weighting of the phase coherence imaging technique is more effective.

Various techniques can be used to shorten this time-domain signal. In one embodiment, the time-domain signal is shortened by splitting the transmit signal using a newly developed "split aperture" technique. In the split aperture technique, the aperture is divided into a number of sub-apertures, which are then selectively focused to obtain beamformed transmit pulses that shorten the length of the time-stretched signal in the grating lobe region. In another embodiment, the time-domain signal is shortened using a defocused "probing pulse" technique. Any suitable technique known in signal processing for shortening the time-domain signal can be used to enable the use of transmit beamforming with the phase coherence imaging technique, which may be implemented in an ultrasound imaging system.

Accordingly, various aspects of the present disclosure suppress grating lobes in large pitch arrays without requiring synthetic aperture beamforming. Using this technique for suppressing grating lobes, it is possible to develop ultrasound imaging systems having array-based transducers with a larger pitch. The larger pitch may simplify the fabrication procedure of high-frequency transducers significantly, or reduce the number of required elements in 2D arrays resulting in arrays that can beam-steer to lager angles with fewer elements.

BRIEF DESCRIPTION OF THE DRAWINGS

FIG. 1(A) shows a schematic representation of conventional transducer array having a linear array geometry. FIG. 1(B) shows a schematic representation of conventional transducer array having a two-dimensional array geometry. FIG. 1(C) shows a schematic representation of conventional transducer array having an annular array geometry.

DETAILED DESCRIPTION

Figure 2:
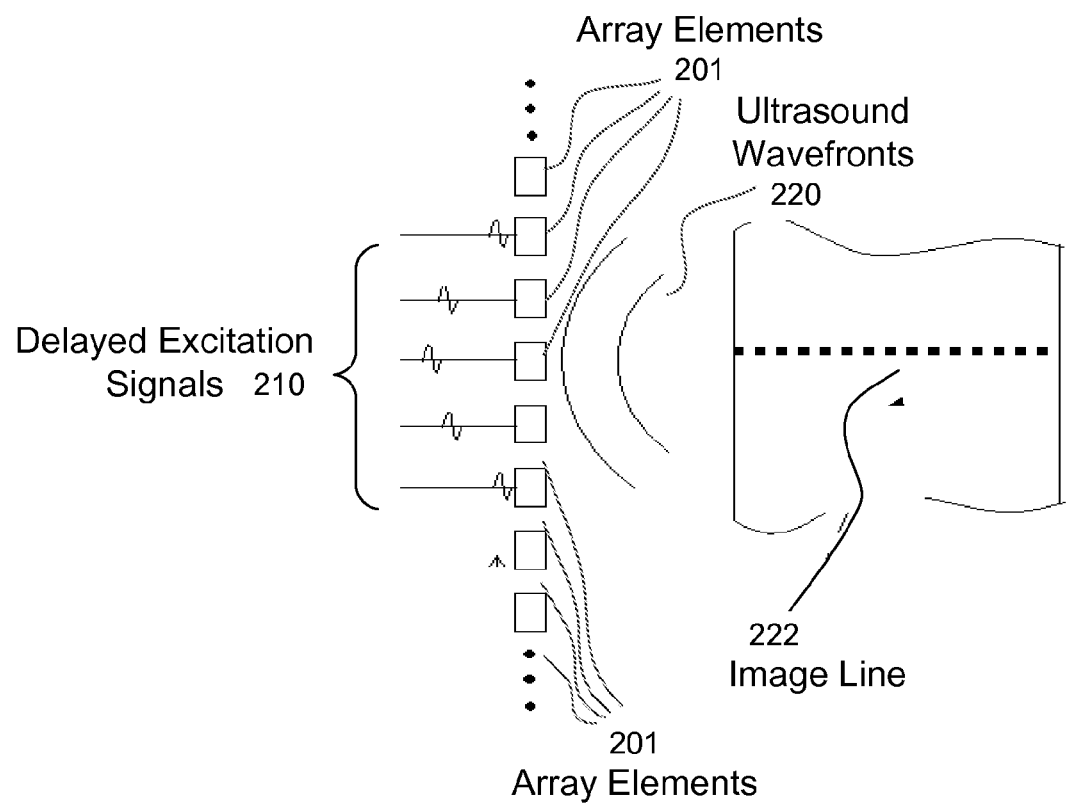
FIG. 2 shows a schematic representation of beamforming using a linear array.

The present disclosure relates generally to systems and methods for effectively reducing the temporal length of transmit grating lobe signals in received ultrasound echoes. The grating lobe signals can then be suppressed using a suitable signal processing method. These methods and systems advantageously make possible the performance of high-frequency and/or 2D ultrasound imaging arrays and provide significant improvements in ultrasound image quality.

A small element-to-element pitch (~0.5λ) is conventionally required for phased array ultrasound transducers in order to avoid large grating lobes. This constraint can introduce many fabrication difficulties, particularly in the development of high-frequency phased arrays at operating frequencies greater than 30 MHz. The present disclosure provides a novel transmit beamforming technique that enables the performance of high-frequency ultrasound imaging.

In various aspects, the present disclosure provides methods for high frequency ultrasound imaging using a split transmit aperture, the method comprising the steps of: splitting a transmit beamformer comprising a phased array of N transmit elements into K sub-apertures, each sub-aperture having N/K transmit elements; forming a focused ultrasound transmit beam from one of the sub-apertures of the transmit beamformer; transmitting the transmit signal towards a target along a focused line of sight; obtaining samples of reflections of the transmit signal from a target at all N elements of the full transmit aperture; and processing the samples to produce an image of the target.

The present transmit beamforming technique can be used in conjunction with any suitable signal processing method, such as for example, phase coherence imaging with sign coherence factor (SCF) receive beamforming (Camacho et al., IEEE Trans UFFC, 56(5):958-974 (2009)), which is capable of suppressing grating lobes in large-pitch phased-array transducers.

In various aspects, methods are provided for splitting the transmit aperture (N elements) into N/K transmit elements and receive beamforming on all N elements to reduce the temporal length of transmit grating lobe signal. This method eliminates the need to use synthetic aperture beamforming in phase coherence imaging. In certain aspects, the received signals are weighted by the calculated SCF after each transmit-receive event to suppress the grating lobes. After pulsing all sub-apertures, the RF signals can then be added to generate one line of the image. Simulated 2-way radiation patterns for different K values have shown that grating lobes can be suppressed significantly at different steering angles. In some aspects, the present disclosure provides techniques for determining the optimal transmit sub-apertures has been developed.

Transducer Arrays

The structure of an array transducer is similar to that of single element transducers in many ways. For example, array transducers are composed of a piezoelectric sandwiched between a lossy backing layer and a matching layer(s). The piezoelectric resonator in an array transducer, however, is diced to produce a series of individual array elements. FIGS. 1(A), 1(B), and 1(C) illustrate the front faces of three common array geometries. The array shown in FIG. 1(A) is a linear array, the array shown in FIG. 1(B) is a two-dimensional (2-D) array, and the array shown in FIG. 1(C) is an annular array.

Linear array transducers, such as the example shown in FIG. 1(A), have the ability to focus the ultrasound energy at any depth in the tissue, along a line parallel to the row of array elements. The ability to focus ultrasound energy at any depth in the tissue makes linear array transducers more attractive than single element transducers because the depth of field is greatly increased. The ultrasound beam is passively focused in the elevation direction (perpendicular to the row of elements) using an acoustic lens or geometric curving. There are two types of linear arrays: one referred to as a "linear array" and the other referred to as a "phased array."

"Linear arrays" focus the ultrasound beam perpendicular to the array using a sub-aperture of array elements. FIG. 2 illustrates a group of array elements 201 used to form an active aperture. The group of array elements are excited using a pattern of delayed excitation signals 210 to produce ultrasound wavefronts 220 that are focused along an image line 222 perpendicular to the array. Additional image lines are obtained by shifting the active aperture across the array. A sub-aperture of elements steps across a much larger aperture, collecting the parallel A-scans needed to produce a 2-D image. A typical linear array will have a total aperture consisting of 256 elements, and use a sub-aperture of 64 elements with wavelength spacing $\lambda$ between the array elements 201.

Figure 3:
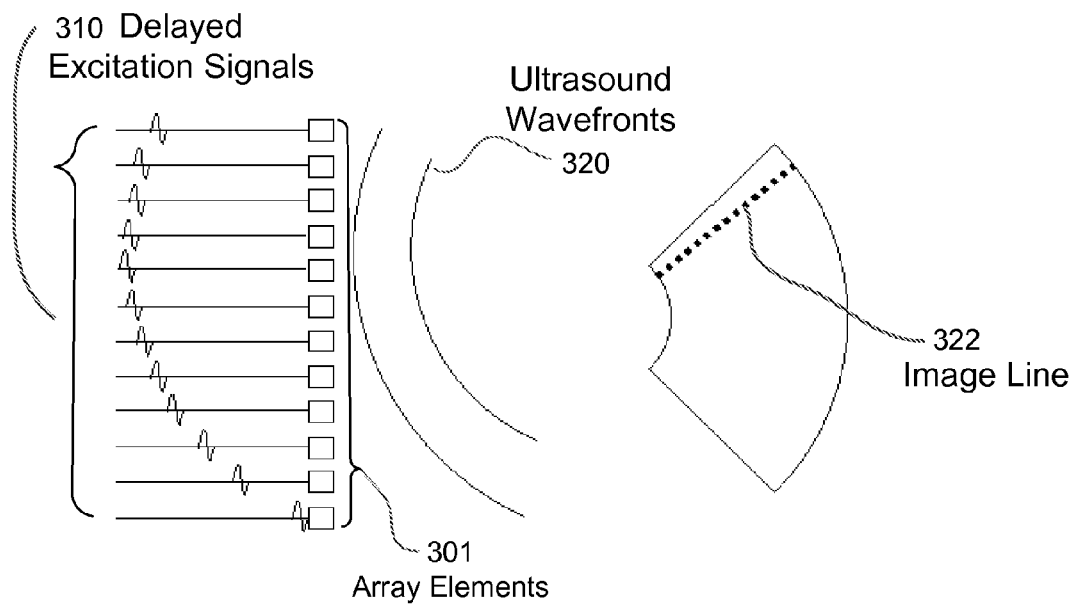
FIG. 3 shows a schematic representation of beamforming using a phased array.

FIG. 3 illustrates the second version of a linear array, the "phased array," that has the ability to steer the ultrasound wavefronts 320. The elements 301 in the phased array are excited using a pattern of delayed excitation signals 310 that focuses and steers the ultrasound wavefronts 320. Consequently, the image line 322 is no longer perpendicular to the array. Additional image lines are obtained by changing the steering angle. By steering the ultrasound beam at different angles, a series of A-scans are collected. These A-scans are used to generate a sector format image. As a result, phased arrays can have a large field of view with a relatively small aperture. Typically, a phased array will use 128 elements with half-wavelength spacing between the array elements 301. Generally, other than the smaller element spacing and aperture size, phased arrays are similar to linear arrays.

Although annular arrays, such as the example shown in FIG. 1(C), are suitable for many topical applications in high-frequency imaging, due to their relatively large element sizes and low element counts, they do not have the ability to beam steer or translate the aperture electronically and therefore need to be mechanically scanned. This means that the fixed aperture needs to be relocated in space in order to generate the parallel "lines of sight" that make up a 2D image. This creates a larger "effective" aperture limiting the packaging size, image scan window, and frame rate. High-frequency linear phased array transducers can overcome many of the problems inherent to annular arrays. For example, since phased arrays require no aperture translation arrays that are 3 mm or less in total aperture can be manufactured.

Transmit Beamforming

It is convenient to separate an ultrasound beamformer into two parts: the transmit beamformer, which generates the sequence of high voltage pulses required to excite the array and focus the transmitted energy; and the receive beamformer, which focuses the received signals. The operation of the transmit beamformer will be described with reference to FIG. 4.

Figure 4:
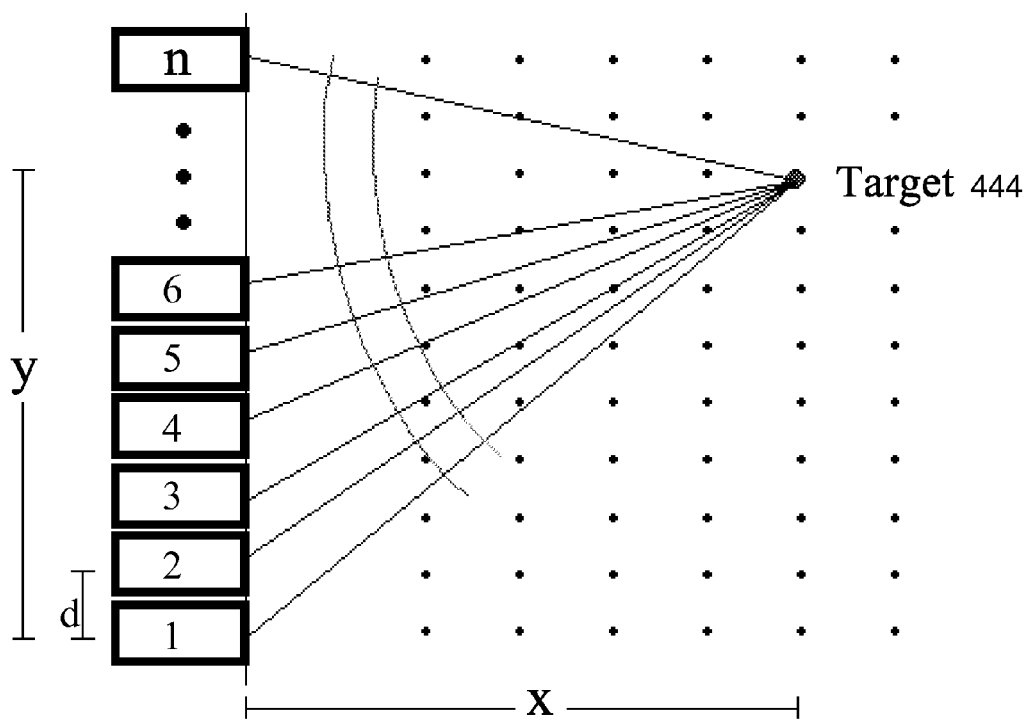
FIG. 4 shows a schematic representation of a geometrical arrangement of an array and a desired focal point within an imaging medium.

FIG. 4 illustrates a geometrical arrangement of an array of elements 1 through n (in cross-section) that are each separated by a distance d, and a desired focal point, target 444, within an imaging medium. The lines connecting the transducer array elements 1 through n to the target 444 show the paths from each element to the target 444. In order to focus the transducer radiation to a target 444, the path length distances from each of the transducer elements 1 through n to the target 444 must be determined. Then the delay pattern to apply to signals to the transducer elements 1 through n that is required to focus the sound waves to the target 444 can be determined.

The path length from each of the transducer elements 1 through n to the target is calculated based on geometric analysis.

$$l_n(x,y) = \sqrt{(y-d_n)^2 + x^2} \qquad \text{Eqn. (1)}$$

In Equation (1), $l_n$ is the distance from the nth transducer element to the desired (x,y) coordinate. If a constant speed of sound within the medium is assumed, the total time it takes a pulse to travel from the nth transducer element to the target is $l_n/c_o$, wherein $c_o$ is the assumed speed of sound within the medium.

In order to create constructive interference at the desired focal distance, a delay pattern is inserted so that all the pulses from transducer elements 1 through n arrive at the target 444 at the same time. These delays are calculated by subtracting the maximum element to target flight time given by Equation (2).

$$\Delta \tau_n(x, y) = \frac{\sqrt{(y-d_n)^2 + x^2}}{c_o} - \frac{\sqrt{y^2 + x^2}}{c_o} \qquad \text{Eqn. (2)}$$

In Equation (2), $\Delta\tau_n$ corresponds to the excitation delay for element n. Because a transmit beamformer can only focus at one depth for each transmit event, the transmitted wave is allowed to disperse before subsequent transmit pulses are applied.

Receive Beamforming

Figure 5:
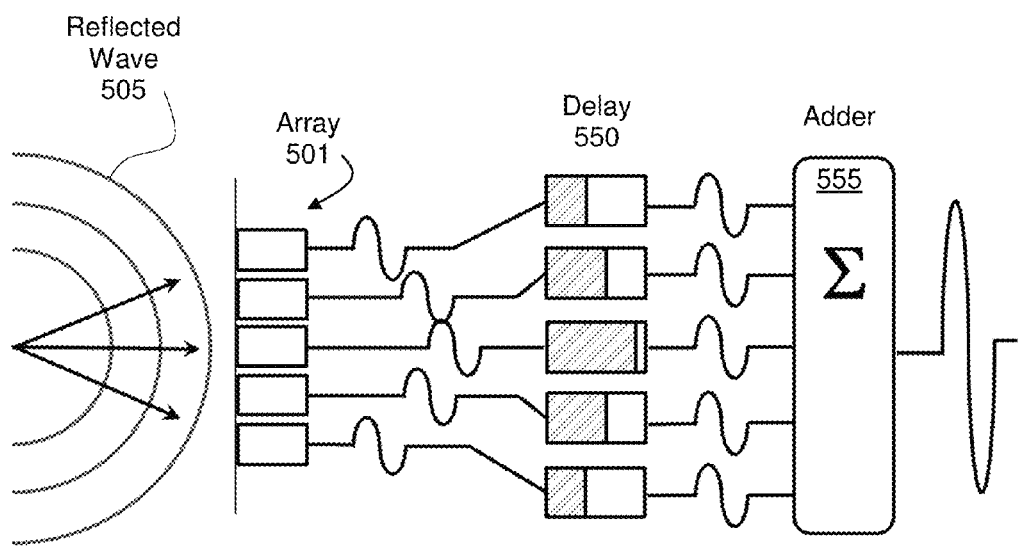
FIG. 5 shows a schematic representation of receive beamforming.

Analogous to the transmit beamforming; the radiation pattern that is received by the array can also be focused. The echo from a small object in the body will arrive back at different array elements at slightly different times. By delaying the signals from different elements to account for the difference in arrival times, the echoes can be re-aligned so that they will add coherently. A flow diagram of receive beamforming is shown schematically in FIG. 5. The transducers (array elements 501) receive the reflected wave 505 and the signals produced are delayed in a phased pattern using delay devices 550 to create constructive interference upon summation at adder 555.

The receive beamforming process is similar to transmit focusing with a difference: in transmit focusing, pulses can only be focused to one depth in the tissue at a time, whereas in receive beamforming it is possible to dynamically change the delay pattern applied to the echoes as they are received. In a sense, receive beamforming allows one to approximate the radiation pattern of a geometrically shaped transducer whose geometric focus is sweeping forward at the speed of sound. Like transmit beamforming, the delay pattern for the transducer elements in the array 501 is related to the time of flight between the element and the target.

Phased Array Transducers

Phased array transducers can provide a large field of view with a small aperture. However, a small pitch (~0.5$\lambda$) is conventionally required for phased array transducers in order to avoid large grating lobes. This produces huge fabrication challenges for high frequency phased arrays. The present disclosure provides a novel method for ultrasound imaging in which splitting the transmit aperture into K sub-apertures generates broader band grating lobe echoes. By applying a suitable signal processing method, such as for example, the previously described SCF weighting coefficients, grating lobes can be significantly suppressed over a conventional transmit beamforming technique with large pitch arrays. Using basic geometric principles, an expression for the optimal aperture splitting location can be derived that will produce equally short transmit pulses in the grating lobe region for the different sub-apertures. Splitting the aperture into equal-width sub-apertures closely approximates the optimal splitting locations for most f-numbers and grating lobe angles. According to the present disclosure, the use of a larger number of sub-apertures (K) can increase the amount of grating lobe suppression for different pitches and steering angles. By increasing the steering angle, greater values of K are required for acceptable grating lobe suppression. Therefore, the number of split apertures (K) should be chosen based on the steering angle and desired image contrast (grating lobe level) for the individual application. The present methods enable high-frequency phased array transducers to be developed with larger element-to-element pitch, which simplifies device fabrication significantly.

High-frequency ultrasound imaging (i.e., >20 MHz) can provide high resolution images of micro-scale tissue structures (Lockwood et al., Ultrasound in Medicine and biology, 15(6):60-71 (1996)). The current commercially available systems are mostly limited to intravascular and small animal imaging applications. The relatively slow expansion into new clinical applications of high-frequency ultrasound can mostly be attributed to the difficulties in developing array-based transducers and beamformers operating at these frequencies. Conventionally, high-frequency ultrasound imaging systems have been based on single-element transducers, which introduce a trade-off between lateral resolution and depth-of-field. Mechanical aperture translation is also needed in this case to capture a full 2D image. Recent effort has focused on the development of high-frequency annular and linear array transducers (Cannata et al., IEEE Trans UFFC, 53(1):224-236 (2006); Brown et al., IEEE Trans UFFC, 51(8):1010-1017 (2004); Brown et al., IEEE Trans UFFC, 54(9):1888-1894 (2007); Lukacs et al., Proc IEEE UFFC, 105-108 (2005); Ritter et al., IEEE Trans UFFC, 38(2):48-55 (2002); Ketterling et al., IEEE Trans UFFC, 52(4):672-681 (2005); Snook et al., Proc IEEE Ultrason Symp, 1:865-868 (2003); Hu et al., Proc IEEE Ultrason Symp (2009); Sisman et al., Proc IEEE Ultrason Symp (2009)). Although high-frequency annular arrays have been shown to provide large depth-of-field and high-quality images, they also require mechanical spatial translation, which can limit the frame rate and packaging size. The development of high-frequency linear array transducers has proven to overcome limitations in frame-rate previously introduced by the mechanical translation, however, the field-of-view and packaging size is limited to the size of the full aperture since linear arrays can only focus the ultrasound beam perpendicular to the array and do not have the ability to beam-steer. In order to overcome the tradeoff between field-of-view and packaging size, the development of a high-frequency curvilinear array has recently been reported (Hu et al., Proc IEEE Ultrason Symp (2009)). Although arrays such as these are indeed promising, a more efficient method of overcoming the tradeoff between field of view and aperture size can be achieved with a phased array transducer.

Phased array transducers have the ability to beam-steer and do not need to electronically translate a sub-aperture in order to generate parallel A-scan lines. Unfortunately, developing high-frequency phased array transducers has proven to be extremely difficult due to the difficulties in fabrication. Specifically, in order to steer the ultrasound beam, the element-to-element pitch needs to be significantly reduced in order to avoid the introduction of grating lobes (Cobbold, Foundations of biomedical ultrasound, 437-450 (2007)). For example, at 50 MHz and a steering angle of 45 degrees, in order to push the grating lobe angle to 90 degrees, the element pitch needs to be reduced to 15 microns (Ziomek, Fundamentals of acoustic field theory and space-time signal processing, 528-532 (1955)), which is beyond most current fabrication capabilities. For this reason, many studies have investigated different methods for grating lobe suppression to allow design of phased arrays with larger pitch (Rew et al., Electronics letter, 19(19):1729-1731 (1993); Gavrilov et al., IEEE Trans UFFC, 44(5):1010-1017 (1997); Wang et al., IEEE Trans Antennas and Propagation, 56(6) (2008); Ustuner et al., U.S. Pat. No. 7,207,942 B2 (2007); Li et al., IEEE Trans UFFC, 50(2):128-141 (2003)).

Grating Lobe Suppression

Any suitable signal processing method for suppressing grating lobes can be used according to the present disclosure, including methods currently described in the literature for suppressing grating lobes in large-pitch phased array transducers. According to various aspects of the present disclosure, the processing method comprises weighting the samples by a calculated phase coherence factor, which can comprise SCF.

One suitable signal processing method focuses primarily on manipulation of the array structure by removing the periodic pattern of the elements (Rew et al., Electronics letter, 19(19):1729-1731 (1993); Gavrilov et al., IEEE Trans UFFC, 44(5):1010-1017 (1997); Wang et al., IEEE Trans Antennas and Propagation, 56(6) (2008)). In these methods, some elements are removed randomly until an under-sampled portion of the aperture remains, resulting in a "sparse array." However, there is a reduction in transmit intensity of sparse arrays because of the low number of elements, which results in a low signal-to-noise ratio (SNR). The other major drawback to sparse arrays is that the level of the side lobes will increase because the average side lobe to main lobe power is equal to 1/N (Cobbold, Foundations of biomedical ultrasound, 437-450 (2007)).

According to one aspect of the present disclosure, the signal processing method can comprise a method for suppressing grating lobes that focuses on processing the echoes received by each element to suppress grating lobes. According to these methods, a weighting factor (between 0-1) is calculated based on a specific characteristic of echoes such as time-shift (cross-correlation (Ustuner et al., U.S. Pat. No. 7,207,942 B2 (2007))) or the receiving direction of the echoes (FFT (Li et al., IEEE Trans UFFC, 50(2):128-141 (2003))). The echoes are multiplied by the computed weighting factors and added to generate one line of the image. Although these methods are promising, they have the inherent drawback of high computational cost in calculating the weighting factors, which makes them unsuitable for high frame-rate imaging.

According to one aspect of the present disclosure, the signal processing can comprise a low-computational power method called "phase coherence imaging" for grating lobe suppression in large pitch arrays (Camacho et al., IEEE Trans UFFC, 56(5):958-974 (2009)). In this method, the phase of delayed echoes received by each element is detected and then a weighting factor is defined based on the standard deviation of the phases at each time point. At the focal point, all of the element echoes will be in phase, so the standard deviation of their phases is close to zero, which results in a weighting factor close to one. For the grating lobes, the phases of the echoes are not always perfectly in phase, so the standard deviation of them in certain cases is greater than zero, resulting in a lower weighting factor. This method is mostly effective for synthetic aperture beamforming where the received grating lobe echoes are broadband. Essentially, after the transmit beamforming delays are reconstructed along with the receive beamformed A-scans, time domain points that are similar to the main lobe are either zero or random in phase over a large number of the elements. This creates a spread in the standard deviation of phases and therefore the broad bandwidth of the received echoes is the primary reason that the standard deviation of the phases is non-zero.

Shortening Transmit Grating Lobe Signals

The present disclosure provides novel methods for generalizing the phase coherence imaging method for suppressing grating lobes of phased array transducers when using transmit beamforming, where long narrowband grating lobe echoes are inevitable. The present disclosure relates generally to systems and methods for effectively reducing the temporal length of transmit grating lobe signal in received ultrasound echoes. The benefits of grating lobe suppression through signal processing are significantly improved by decreasing the time-domain signal of the grating lobe signal prior to signal processing. Using these methods, phased arrays with element pitches much larger than one-half of the ultrasound signal wavelength are possible. Therefore, the fabrication of high-frequency phased arrays is significantly simplified, and the number of elements required in 2D arrays is reduced.

A special case of phase coherence imaging is calculating sign coherence factor (SCF) as the weighting factor. In this method, the sign bit of received echoes by each element ($b_i$) at each time point is considered (Camacho et al., IEEE Trans UFFC, 56(5):958-974 (2009)). At each time point, the standard deviation of sign bits ($\sigma$) is calculated and the SCF is defined as follows in Equations (3A) and (3B):

$$SCF^\alpha = |1-\sigma|^\alpha \quad \text{Eqn. (3A)}$$

$$\sigma = \sqrt{1 - \left[\frac{1}{N}\sum_{i=1}^{N} b_i\right]^2} \quad \text{Eqn. (3B)}$$

Where $\alpha \geq 1$ adjusts the sensitivity of the correction factor and N is the number of elements. Although it has been shown that different "$\alpha$" values can actually further suppress grating lobes, for the remainder of this article we assume an $\alpha$ value equal to 1. At the focal point, where all of the received echoes are in phase, the sign bits of all elements are the same, resulting standard deviation close to zero and as a consequence the weighting factor equal to one. When transmit beamforming is used, the signal in the grating lobe region in a one-way radiation pattern is very long in the temporal domain. Therefore, when considering echoes received by the array elements from the grating lobe region, they are also very long and narrowband. Even after the beamforming delays are inserted, these long grating lobe echoes overlap and if the sign bit is considered in the same temporal region as the main lobe signal, the signals are all similar in phase and hence the weighting factor in this case is also approximately equal to 1.

By shortening the time-domain of the grating lobe signals, the present method makes possible the performance of high-frequency ultrasound imaging at greater image resolution. Using the present methods, it is possible to perform the method at ultrasound frequencies greater than 30 MHz. In some aspects, the method can be performed at frequencies of 20 MHz, 30 MHz, 40 MHz, or 50 MHz. The present methods are also applicable to low frequency ultrasound, such as at frequencies below 20 MHz.

Figure 6A:
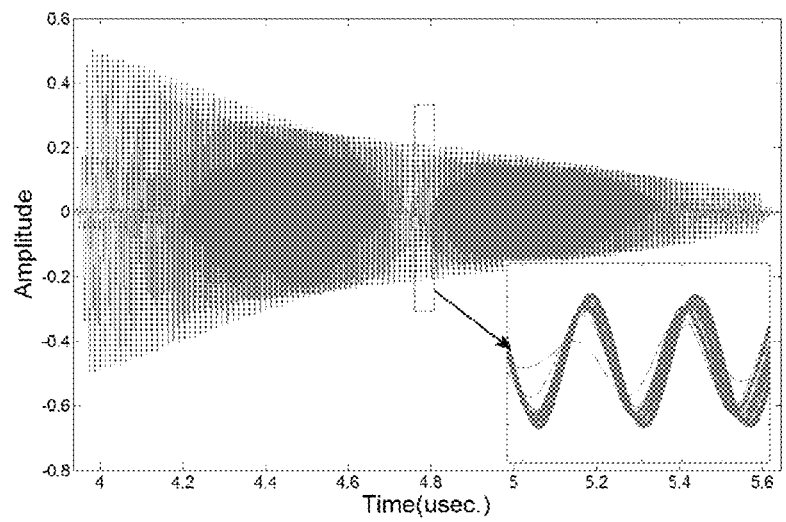
FIG. 6 shows a comparison of grating lobe echoes for a 64 element phased array with 1.25λ pitch using (A) transmit beamforming, (B) synthetic aperture pulsing with only the central element, and (C) split-aperture transmit beamforming K=2). The receive beamforming delays have been inserted.

FIG. 6(A) shows an example of the individually received echoes from the grating lobe region resulting from transmit beamforming. The signals are for a 64 element phased array with an element pitch of 1.25λ steering at an angle of 25 degrees and focusing to f/2. The pulse echoes were simulated using the two-way impulse response method (San Emeterio et al., J Acoust Soc AM, 92(2):651-662 (1992)). The sum of the one-way transmit pulses in the grating lobe region is calculated and then used as the point source for the received echoes. The bandwidth of the two-way pulse echo in the main lobe region however is approximately 50%. FIG. 6(A) clearly shows how the overlapping echoes from the grating lobe region are stretched out in the time domain. Because they are virtually all in phase over a temporal window similar to the main lobe, a large weighting factor results. This prevents SCF from effectively suppressing grating lobes when transmit beamforming is used.

Figure 6B:
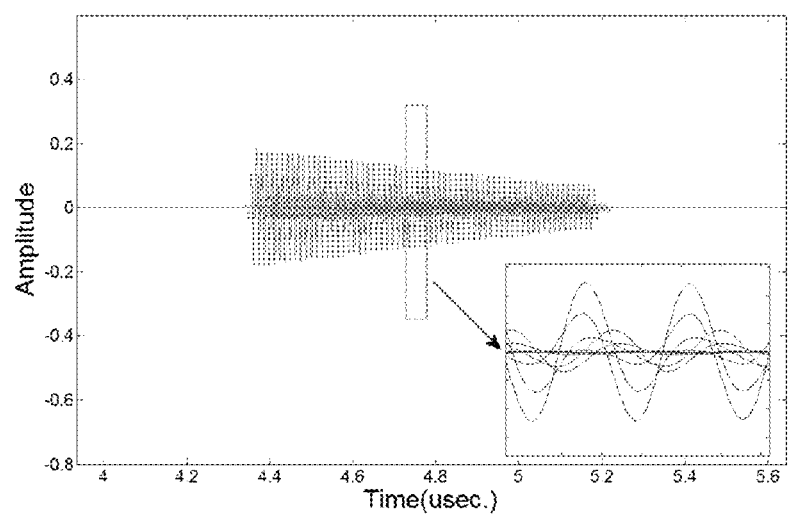

The SCF method can, however, effectively suppress grating lobes when synthetic aperture transmit beamforming is used. The main difference is that for synthetic aperture, only one element is pulsed at a time which results in broadband echoes returning to the array, even from the grating lobe region. After the receive beamforming delays are inserted, these broadband echoes have very small overlap in the time domain resulting a large sign-bit standard deviation since many of the signals are zero (random phase) at any given moment in time. This produces a very low SCF weighting coefficient. FIG. 6(B) shows an example of the received grating lobe echoes from a 64 element, 1.25λ pitch phased array steering to 25 degrees when pulsed with a single defocused element (element 32). In this case, it can clearly be seen that the echoes are predominately not in phase in the same temporal region as the main lobe signal. In fact, the received signals are so broad band that most are zero (random phase).

As addressed above, synthetic aperture beamforming has significant disadvantages because many transmit events are required before the signals are beamformed. Therefore, the pre-beamformed signals are susceptible to phase distortions from small tissue movements during the relatively long pulsing sequence. High-frequency arrays are particularly sensitive to small tissue movements since the wavelengths are extremely short and therefore a small amount of tissue motion results in a large change in the echo phase. Transmit beamforming avoids these phase distortions because long pulsing sequences between beamforming are not required. The methods of the present disclosure advantageously shorten the time-domain of grating lobes without requiring the use of synthetic aperture beamforming.

Figure 7A:
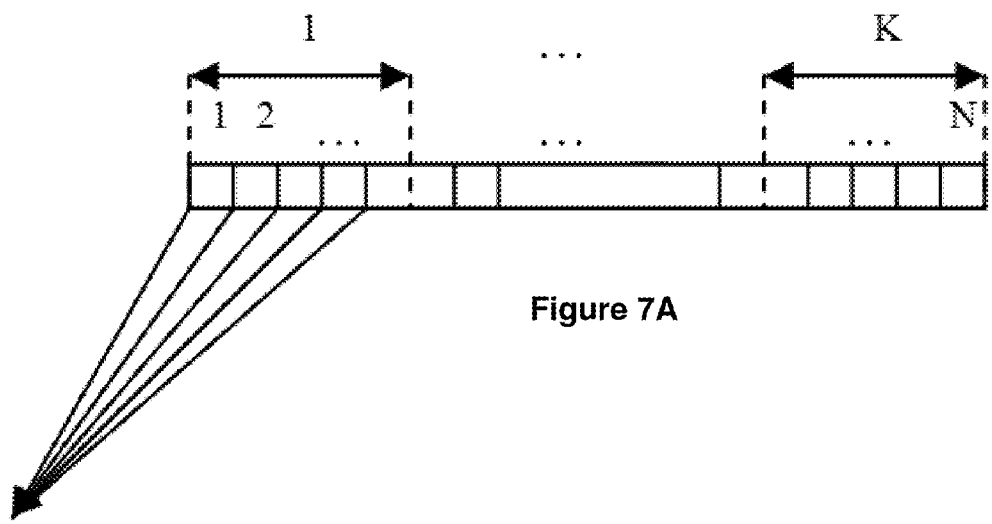
FIG. 7 shows proposed transmit and receive apertures according to various aspects of the disclosure. Each sub-aperture (K) is focused separately during transmission (A) and the echoes are received by all elements (B). One line of the image is constructed after all sub-apertures are pulsed.

If transmit beamforming is desired for large pitch phased arrays however, a new method for increasing the effectiveness of the SCF is needed. Since the underlying problem in applying SCF to an array using transmit beamforming is the long time-stretched signal resulting in the grating lobe region, a method that produces shorter time-domain signals should result in a smaller number of the received echoes overlapping upon receive and hence the SCF weighting technique should be more effective. Since the length of the time domain signal is approximately equal to the difference in arrival times between the closest and furthest elements in the array, we are proposing a very simple solution of splitting the transmit aperture into K sub-apertures, where K potentially varies from 2 to N (number of elements) in order to shorten the length of the time-stretched signal in the grating lobe region (FIG. 7(A)). It is desirable to keep K as low as possible in order minimize the total amount of time expired before the signals are beamformed. Again, this reduces the amount of phase aberration between pre-beamformed signals due to tissue motion.

According to the present disclosure, the number of sub-apertures (K) can be any value such that the transmit aperture is capable of producing a focused beam. In certain aspects, K is an integer between 2 and 16. In further aspects, K is between 2 and 10. In yet further aspects, K is 2.

Any suitable element-to-element pitch can be used according to the present methods. According to certain aspects, the element-to-element pitch is greater than $0.5\lambda$. In further aspects, the element-to-element pitch is $0.5\lambda$. In certain aspects the element-to-element pitch is $0.75\lambda$. In certain aspects the element-to-element pitch is $1\lambda$. In certain aspects the element-to-element pitch is $1.25\lambda$.

Any suitable steering angle can be used according to the present methods, depending on the value of the corresponding element-to-element pitch. According to various aspects, the steering angle can be from 1 to 45 degrees. In certain aspects, the steering angle is 10 degrees. In further aspects, the steering angle is 15 degrees. In further aspects, the steering angle is 20 degrees. In further aspects, the steering angle is 25 degrees. In further aspects, the steering angle is 35 degrees. In further aspects, the steering angle is 40 degrees. In further aspects, the steering angle is 45 degrees.

According the present disclosure, any suitable array size (N) can be used, for example and without limitation, the array size (N) can be between 16 and 512.

Figure 6C:
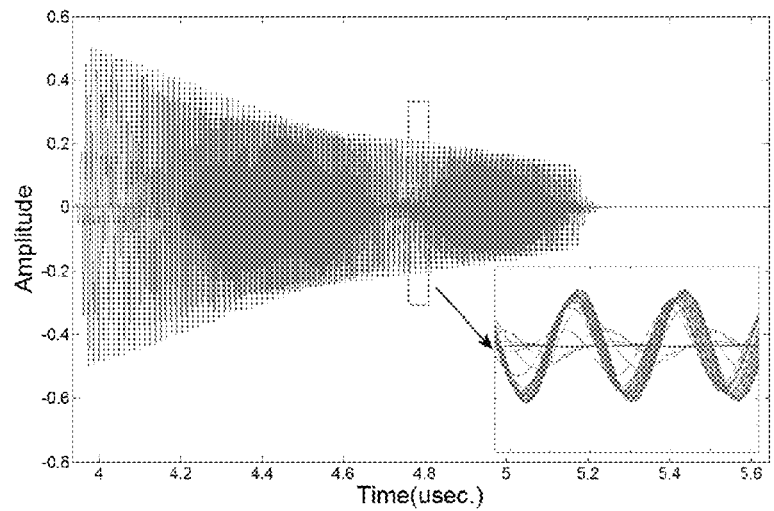
Figure 7B:
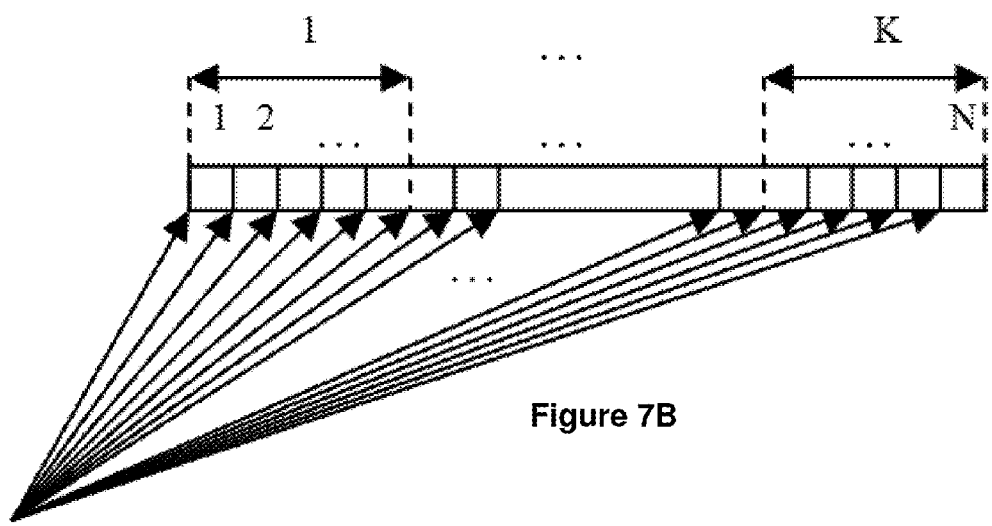

Unlike synthetic aperture beamforming which uses defocused pulses, the methods of the present disclosure use transmit focusing along different lines of sight. In this case, N/K elements are pulsed with transmit focusing delays and all N elements participate in the receive aperture (FIG. 7(B)). After each transmission, the SCF is calculated based on the time-shifted echoes and is used to weight the beamformed signal. After K transmit events, all weighted echoes are added together to generate one line in the image. Again, by reducing the size of the aperture to N/K elements for transmission, the grating lobe signal is shorter due to the reduced difference in distance between the closest and furthest elements in the transmit aperture. This reduction in overlap for the grating lobe echoes results in a much lower SCF. FIG. 6(C) shows an example of the received grating lobe echoes resulting from a split transmit aperture of 32 elements after the receive beamforming delays have been inserted on all 64 receive elements K=2). Similar to FIGS. 6(A) and 1(B), this simulation is for a phased array with an element pitch of $1.25\lambda$, a steering angle of 25 degrees, and a focal depth of f/2. It can clearly be seen from this plot that there is much less phase coherence between the echoes for the split transmit aperture technique and will therefore result in a much lower SCF weighting factor.

Figure 8:
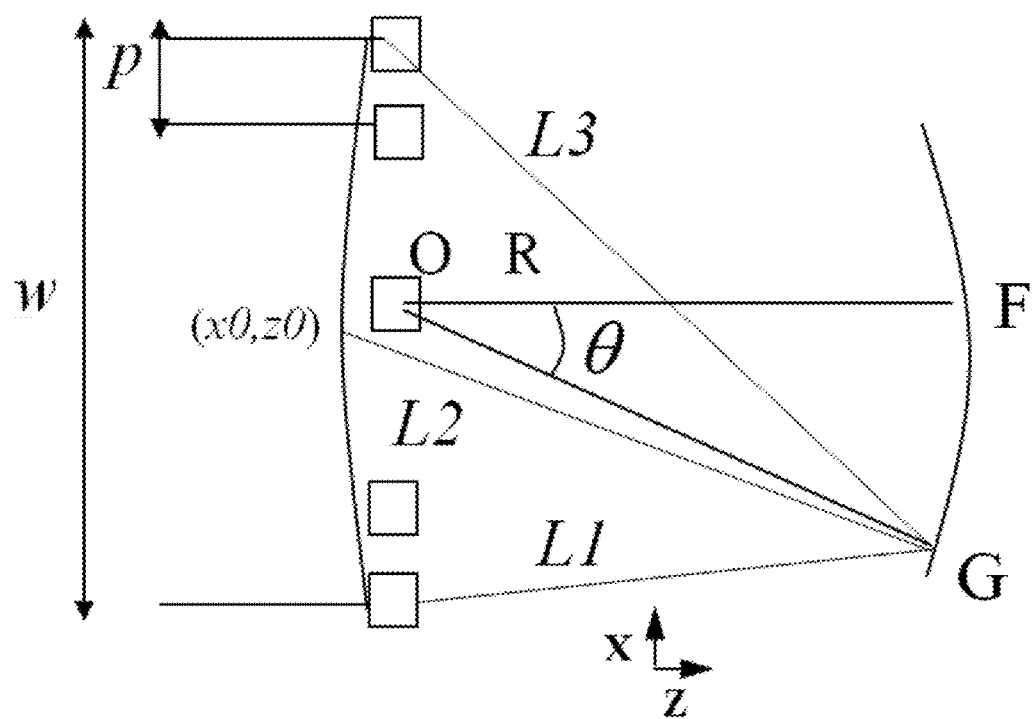
FIG. 8 shows the geometry of a phased array transducer with aperture width (w), and element-to-element pitch (p) focused at focal point (F) on the main axis. The virtual curved aperture is used for calculating the distances between grating lobe point (G) and the aperture points (L1, L2, and L3) in order to account for the beamforming delays.

According to various aspects of the present disclosure, the optimal transmit apertures are determined in order to achieve equally short temporal transmit pulses between sub-apertures in the grating lobe region. Experimental simulation results have showed that approximately equal-width sub-apertures (½*w for K=2, ¼*w for K=4, etc.) produce approximately equally short grating lobe transmit pulses or rather equal differences in distance between the closest and furthest element in the sub-aperture. An expression is derived below for determining where to split the transmit aperture in the case of K=2 in order to obtain equal length grating lobe signals from both transmit apertures. The optimal position occurs when the difference in distance between the closest and furthest elements in each sub-aperture are equal. FIG. 8 shows the geometry of a phased array where "O" is the origin of the x-z Cartesian plane. It has been assumed that the focal point (F) is on the main axis and the grating lobe (G) is located on the same radius (R) at an angle from the central axis calculated by Equation (4) (t'Hoen, IEEE Ultrason Symp Proc, 94-95 (1982)).

$$\theta = \sin^{-1}\left(\frac{\lambda}{p}\right) \qquad \text{Eqn. (4)}$$

In order to account for the effect of an array of elements with transmit beamforming delays inserted in order to focus to F, a virtual curved aperture is considered for the rest of the derivation. L1, L2, and L3 are the distances between the grating lobe point (G) and the points on the virtual curved aperture. In order to have transmit pulses with the same length in the time domain for both splits, the equality of distances defined in (3) should be satisfied.

$$L3 - L2 = L2 - L1 \qquad \text{Eqn. (5)}$$

$$L2 = \frac{(L1 + L3)}{2}$$

where the distances between grating lobe and the virtual aperture points are:

$$L1 = \sqrt{\left(R\sin\theta - \frac{w}{2}\right)^2 + (R\cos\theta)^2} \qquad \text{Eqn. (6)}$$

$$L3 = \sqrt{\left(R\sin\theta - \left(-\frac{w}{2}\right)\right)^2 + (R\cos\theta)^2}$$

$$L2 = \sqrt{(R\sin\theta - x_0)^2 + (R\cos\theta - z_0)^2}$$

where "w" is the total array aperture and $(x_o, z_o)$ is point on the virtual curved aperture. It can be shown that for L2, $z_0$ can be replaced as a function of $x_0$ reducing L2 to:

$$L2(x_0) = \sqrt{(R\sin\theta - x_0)^2 + \left(R\cos\theta - \left(R - \sqrt{R^2 + \left(\frac{w}{2}\right)^2 - x_0^2}\right)\right)^2} \qquad \text{Eqn. (7)}$$

and L1 and L3 are simply $$L2\left(\frac{w}{2}\right) \text{ and } L2\left(-\frac{w}{2}\right)$$

respectively. The following derivation is based on the assumption that $$R \gg \frac{w}{2}$$

which is a reasonable assumption at f-numbers greater than 2. By squaring the right side of Equation (5), we obtain:

$$\frac{\left(\sqrt{\left(R\sin\theta - \frac{w}{2}\right)^2 + (R\cos\theta)} + \sqrt{\left(R\sin\theta - \left(-\frac{w}{2}\right)\right)^2 + (R\cos\theta)^2}\right)^2}{4} \approx R^2 + \frac{R^2\cos^2\theta \frac{w^2}{4}}{\left(R^2 - \frac{w^2}{4}\right)} \quad \text{Eqn. (8)}$$

The approximation is based on the first-order Taylor approximation of a square:

$$\sqrt{x^2 + a} = x + \frac{a}{2x} \quad \text{Eqn. (9)}$$

By squaring the right side of Equation (5), and again using the Taylor approximation in Equation (9), we obtain the expression:

$$(R\sin\theta - x_0)^2 + \left(R\cos\theta - \left(R - \sqrt{R^2 + \left(\frac{w}{2}\right)^2 - x_0^2}\right)\right)^2 \approx \quad \text{Eqn. (10)}$$
$$(1 - \cos\theta)x_0^2 - (2R\sin\theta)x_0 + \left(\cos\theta\frac{w^2}{4} + R^2\right)$$

The equality of Equation (8) and Equation (10) therefore results in $$(1 - \cos\theta)x_0^2 - (2R\sin\theta)x_0 + \left(\cos\theta\frac{w^2}{4} - \frac{R^2\cos^2\theta \frac{w^2}{4}}{\left(R^2 - \frac{w^2}{4}\right)}\right) = 0 \quad \text{Eqn. (11)}$$

By solving the root of Equation (11) and substituting $R = F \cdot w$ and $w = N \cdot p$, the expression for "$x_o$" is obtained, which is the element at which to split the aperture in order to obtain equal-length time-domain signals.

$$x_0 = \left(\frac{F\sin\theta - \sqrt{\frac{F^2\sin^2\theta - (1 - \cos\theta)}{\left(\frac{\cos\theta}{4} - \frac{F^2\cos^2\theta}{(4F^2 - 1)}\right)}}}{(1 - \cos\theta)}\right)(Np) \quad \text{Eqn. (12)}$$

The term $x_o$ is a function of (N, F, p). Generally, however the expression for $x_o$ approaches zero at very large and very small grating lobe angles (i.e., the aperture is split at the central element). Intuitively, one can visualize a pulse arriving at the virtual curved aperture either from 90 degrees or from the main axis. These pulse echoes will "see" a symmetric aperture where the difference between the closest and furthest elements in each sub-aperture (split at $x_o = 0$) are the same. In fact for most grating lobe angles, f-numbers, and element pitches, $x_o$ is typically very close to zero when K=2. In this manner, the transmit beamforming technique is simplified making it easy to implement into a real time system. Similar expressions can easily be obtained for splitting the aperture into 3, 4, 5, or any other suitable value based on these simple geometric principles. Generally, however, splitting the aperture into equally sized sub-apertures closely approximates the calculated value.

Using the "equal aperture split" generalization, the "x" location that should be chosen for spit-aperture transmit beamforming is:

$$\begin{cases} x_i = (i+1)\frac{w}{K} - \frac{w}{2}, & 0 \le i < \frac{K-2}{2} \\ x_i = -x_{(K-2)-i} \\ x_{\frac{(K-2)}{2}} = 0 & \text{if } (K-1) \text{ is odd} \end{cases} \quad \text{Eqn. (13)}$$

where, i is element number, K is the number of splits, w is the width of aperture, and $x_i$ is the coordinate of element based on the geometry in FIG. 8. It should be noted however that the derivation of Equation (12) was based on an approximation that is valid for f-numbers greater than approximately 2. In various aspects, f-numbers greater than 1 are suitable for use with the present methods. In certain aspects, a focal dept of f/2 can be used.

By shortening the time domain of the grating lobe signals as described above, suppression of the grating lobes is dramatically improved using signal processing methods. In various aspects, the grating lobe signal can be suppressed by between 20 dB and 60 dB. In certain aspects, the grating lobe signal can be suppressed by 20 dB. In certain aspects, the grating lobe signal can be suppressed by 40 dB. In certain aspects, the grating lobe signal can be suppressed by 60 dB.

Ultrasound Imaging System

In various aspects, the present disclosure provides a system for high-frequency ultrasound imaging using a split transmit aperture, the system comprising: an imaging array comprising a phased array of N transmit elements, the transmit elements divisible into K sub-apertures, each sub-aperture having N/K transmit elements; a transmit beamformer coupled to the imaging array, wherein the transmit beamformer is configured to apply energy selectively to the elements of each of the sub-apertures to focus a transmit signal from the sub-aperture towards a target; a receive beamformer coupled to the imaging array, wherein the receive beamformer is configured to sample a signal received by the imaging array at each of the N elements thereof; and processing circuitry configured to receive the sampled signal and compute an imaged based thereon.

In various aspects, a computer controls the transmit beamformer. The transmit signals can comprise pulsed signals. The transmitted signals reflect off of tissue structures (or target areas) and are received by the elements in the imaging array. These signals received at the imaging array can be directed through amplifiers that are connected between the elements of the imaging array. The digital data is transferred back to the computer for image processing.

According to the present disclosure, the number of sub-apertures (K) in the system can be any value such that the transmit aperture is capable of producing a focused beam. In certain aspects, K is an integer between 2 and 16. In further aspects, K is between 2 and 10. In yet further aspects, K is 2.

Any suitable element-to-element pitch can be used according to the present systems. According to certain aspects, the element-to-element pitch is greater than 0.5λ. In further aspects, the element-to-element pitch is 0.5λ. In certain aspects the element-to-element pitch is 0.75λ. In certain aspects the element-to-element pitch is 1λ. In certain aspects the element-to-element pitch is 1.25λ.

Any suitable steering angle can be used according to the present system, depending on the value of the corresponding element-to-element pitch. According to various aspects, the steering angle can be from 1 to 45 degrees. In certain aspects, the steering angle is 10 degrees. In further aspects, the steering angle is 15 degrees. In further aspects, the steering angle is 20 degrees. In further aspects, the steering angle is 25 degrees. In further aspects, the steering angle is 35 degrees. In further aspects, the steering angle is 40 degrees. In further aspects, the steering angle is 45 degrees.

According the present disclosure, any suitable array size (N) can be used, for example and without limitation, the array size (N) can be between 16 and 512.

Applications

The presently described methods can be used for any suitable application, such as for example endoscopy, which includes without limitation, laproscopic, itra-cardiac, and surgical guidance imaging, and the like. Thus, the high-frequency ultrasound imaging system described herein can improve diagnostics, interventions, and therapeutic monitoring of a variety of disorders. This new diagnostic imaging approach can improve the objectivity and quality of diagnosis in this field of medicine, allowing physicians to apply more precisely targeted interventions.

EXEMPLARY ASPECTS

Example 1

SCF in Combination with Transmit Beamforming and Synthetic Aperture

Figure 9:
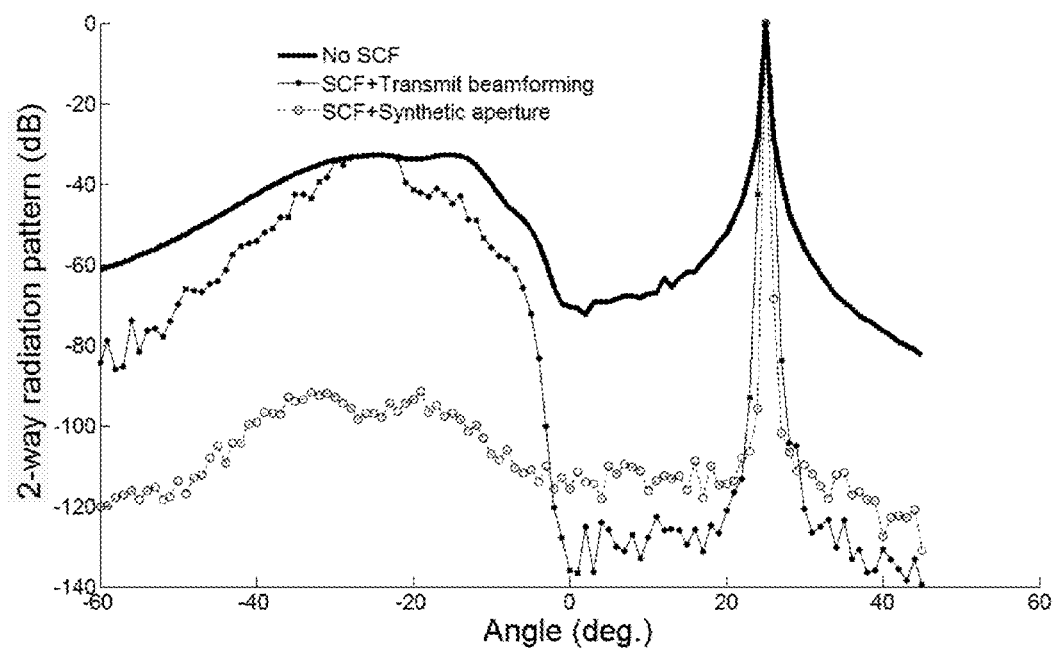
FIG. 9 shows a comparison of grating lobe levels for a 64-element phased array transducer with pitch (p)=1.25λ, focused at f/2, and steered at 25 degrees between no SCF, SCF-weighted transmit beamforming, and SCF-weighted synthetic aperture.

The usefulness of SCF method for grating lobe suppression, is dependent on the temporal length of the transmit pulse in the grating lobe region. The shorter the transmit pulse, the more effective the SCF method is for grating lobe suppression. In FIG. 9, 2-way radiation patterns for a 64-element phased array transducer with element pitch (p)=1.25λ, focused to f/2, steered at 25 degrees are shown. One radiation pattern has no SCF weighting and this is compared with SCF-weighted transmit beamforming K=1) and SCF-weighted synthetic aperture beamforming. It can clearly been seen that SCF weighting is not very effective for suppressing grating lobes when transmit beamforming is used, however, it suppresses the grating lobes in synthetic aperture beamforming more than 50 dB. Again the underlying reason for the big difference in effectiveness between the two transmit techniques is seen in FIGS. 6(A) and 6(B). In FIG. 6(A), the grating lobe echoes in transmit beamforming are all in the same phase whereas they are not for synthetic aperture (FIG. 6(B)). For transmit beamforming, a weighting factor nearly equal to one results in the grating lobe region since all of the sign bits are the same at all time points.

By splitting the aperture into two equal sub-apertures K=2), the signals arriving from the grating lobe region are much shorter and as a result, the received echoes are not completely phase coherent after the receive beamforming delays are inserted. FIG. 6(C) shows the received echoes on all 64 elements and it can clearly be seen that the sign bits are not all similar for the received signals and therefore the SCF weighting factor is low. Similar to the received signals in synthetic aperture beamforming, many of the signals are zero or random in phase at any given time point. By splitting the transmit aperture into more equal width sub-apertures, the length of the grating lobe signals becomes even shorter resulting in an even lower SCF weighting factor.

Example 2

Effect of Aperture Splitting

Figure 10:
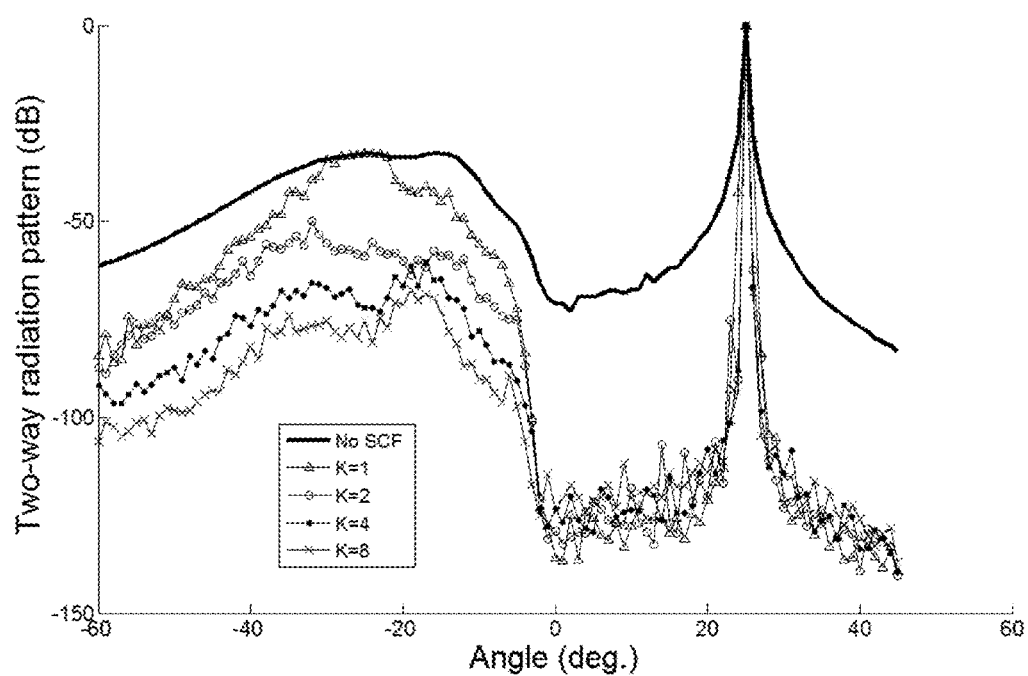
FIG. 10 shows a comparison or grating lobe levels between split-aperture transmit beamforming with different number of splits (K=1, 2, 4, 8). The total aperture is a 64-element transducer with f=40 MHz, pitch (p)=1.25λ, f/2, steered at 25 degrees. As shown by increasing the K, grating lobe is suppressed more while PRF is decreased.

FIG. 10 shows 2-way radiation patterns for a 64-element phased array transducer with pitch (p)=1.25λ, focused at f/2, and steering angle of 25 degrees. Radiation patterns are compared between transmit apertures with no weighting (No SCF), with SCF-weighting and no splitting (K=1), and SCF-weighting+splitting (K=2, 4, 8). This simulation clearly shows that split-transmit apertures are very effective in grating lobe suppression with SCF weighting factors (e.g., 20 dB grating lobe suppression is achieved with K equal to only 2). By increasing K, smaller apertures are pulsed during transmission resulting in shorter grating lobe echoes and as a result have less phase coherence. However, the frame-rate is decreased by increasing K and more transmit events are required before the signals are beamformed, potentially resulting in phase aberrations.

For a more quantitative evaluation of the effectiveness of the split-aperture method on grating lobe suppression, 2-way radiation patterns of 64-element transducers with different pitches (0.75λ, λ, 1.25λ) steered at various angles (0, 15, 30, and 45 degrees) focused at f/2 are processed by SCF-weighting and different split-transmit apertures (K=1, 2, 4, 8). For each pitch value and steering angle, the grating lobe level is plotted versus split-aperture (K) in order to observe the effect of increasing K on grating lobe suppression. Four different steering angles for each pitch value are shown on each graph in FIG. 11, summarizing the results for p=0.75λ, λ, and 1.25λ respectively. At each angle, the grating lobe suppression increases by increasing the number of split-apertures (K). We can see from FIG. 11 that at large steering angles (30, 45 degrees) the amount of grating lobe suppression increases by approximately 20 dB for all element pitches (0.75λ, 1λ, and 1.25λ) by simply splitting the transmit aperture in half (K=2).

Figure 11A:
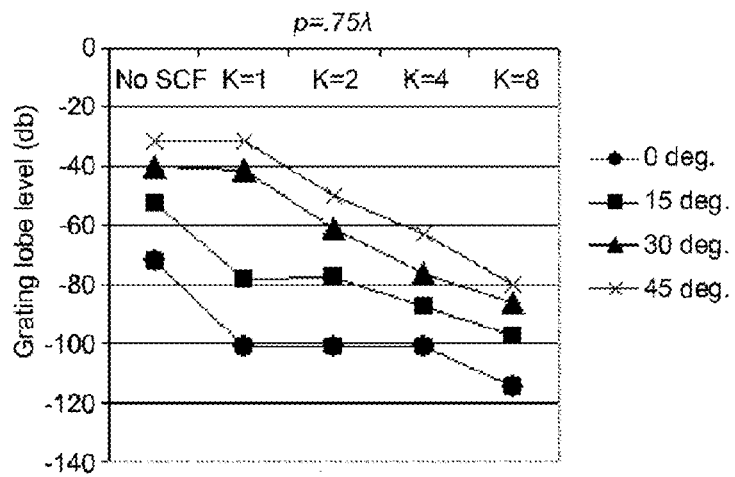
FIG. 11 shows the effect of K sub-apertures on grating lobe suppression for different element pitches and steering angles for a 64-element phased array focused at f/2. The grating lobe level is plotted versus K "splits" (1, 2, 4, and 8) for steering angles 0, 15, 30, and 45 degrees at element pitches of a) p=0.75λ, b) p=λ, and c) p=1.25λ. The regular value of grating lobe with no processing (No SCF) is also plotted for comparison.
Figure 11B:
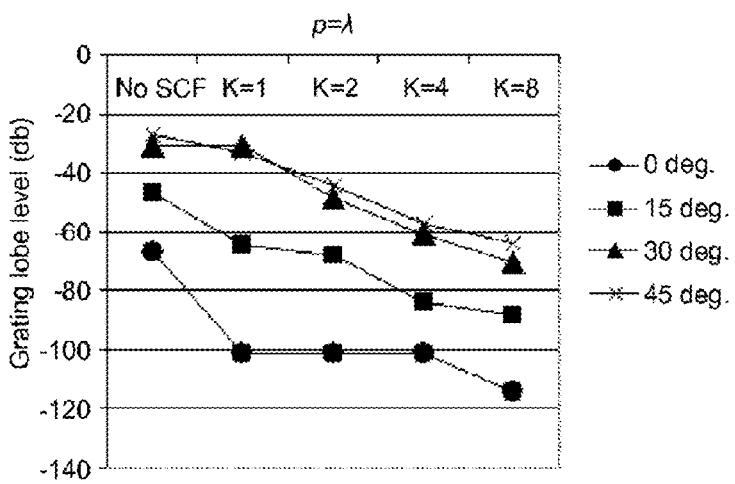
Figure 11C:
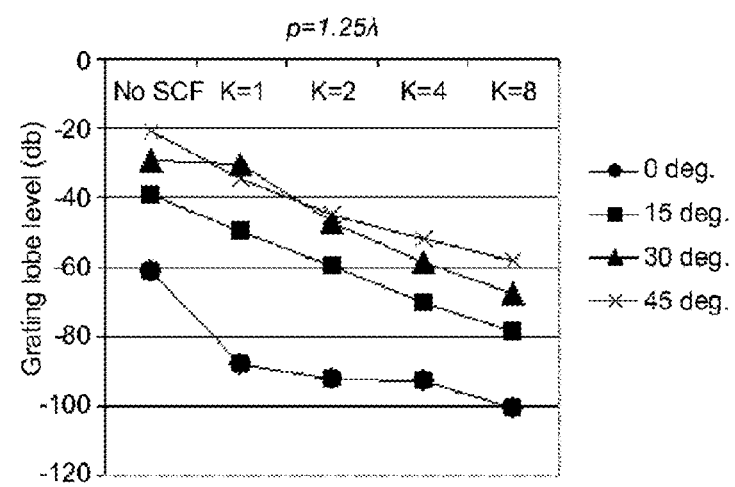

The important aspect of these graphs is that the K value should be chosen based on the range of steering angles in a given application and transducer pitch. For example in the case of p=1λ, FIG. 11(C) shows that with K=1 (SCF-weighting with no splitting), it is possible to suppress the grating lobe to less than −60 dB below the main lobe at a 15 degree steering angle, while for a 45 degrees steering angle, K must be increased to 8 in order to suppress the grating lobes to −60 dB.

As described above, increasing the K decreases the frame rate, which is usually undesirable. Therefore, a split aperture technique that could be used to recoup some of the decreased frame rate would be to gradually increase the "K" value as the A-scan lines shift to larger steering angles. As shown in FIG. 11 even with an element pitch of 1.25λ, SCF weighting will suppress the grating lobe level approximately 60 dB below the main lobe at a zero degree steering angle with K=1 (no aperture splitting). However, by the time 45 degrees of steering is reached, 8 sub-apertures with transmit focusing are required to maintain the same amount grating lobe suppression.

An alternative technique that could potentially avoid the need to use multiple transmit pulses per A-scan line is to send out a broad defocused "probing pulse" from the entire aperture in order to generate a map of SCF values for all space. In order to defocus the pulse, beamforming delays corresponding to a virtual point source behind the array is required (Lockwood et al., IEEE Trans UFFC, 45(4):980-988 (1998)).

The echoes that are received from all points in space are now very broad band (short) and after receive beamforming delays are inserted along different A-scan lines, echoes from the grating lobe regions will have low phase coherence and corresponding SCF weighting factors. Since a broad defocused pulse is used upon transmission, dynamic receive focusing can be performed everywhere and hence a map of SCF weighting factors could potentially be computed and stored in memory for all space from a single probing pulse. Then, if conventional transmit beamforming is carried out (one A-Scan line at a time), the signals can be weighted with the previously computed weighting coefficients from the initial defocused probing pulse. This technique is possible since the weighting coefficients are slowly varying over different regions in space and therefore are not overly susceptible to small amounts of tissue motion during the relatively long pulsing sequence.

Figure 12:
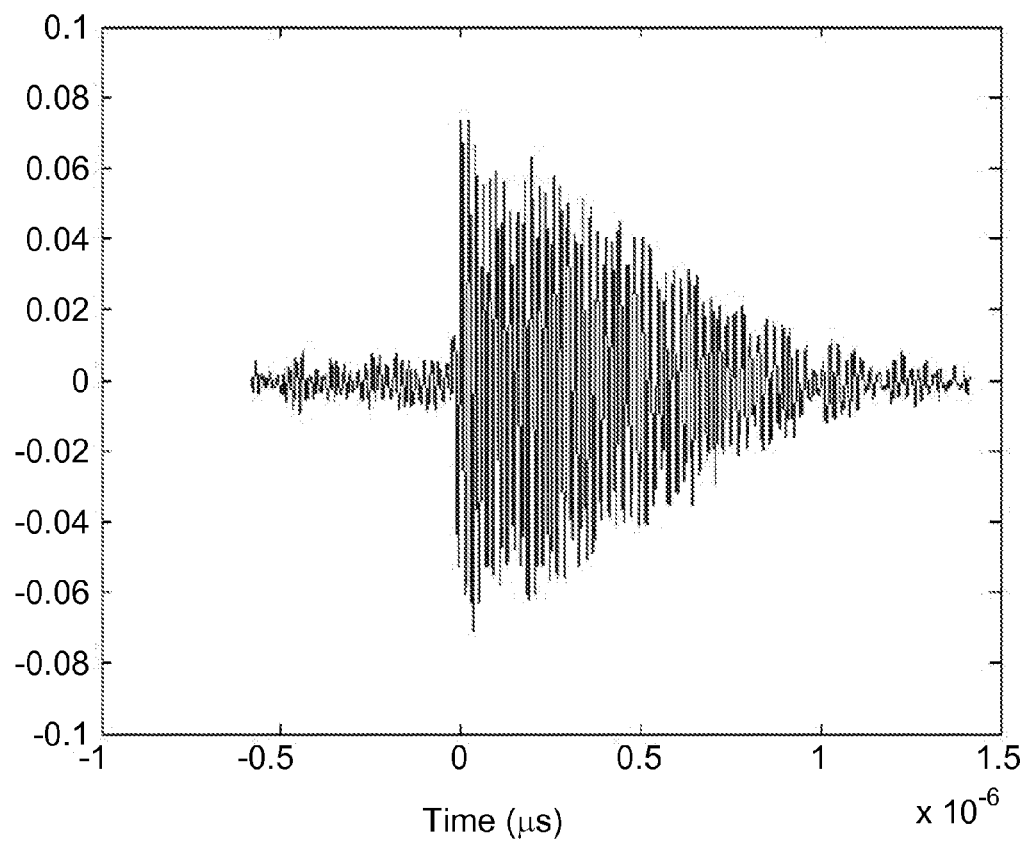
FIG. 12 shows an experimentally measured grating lobe transmit signal when the full 64-element aperture is active and focused off to 25 degrees at f/2. The measurements were obtained using a 64-element 50 MHz phased array with 1.25, element pitch.
Figure 13:
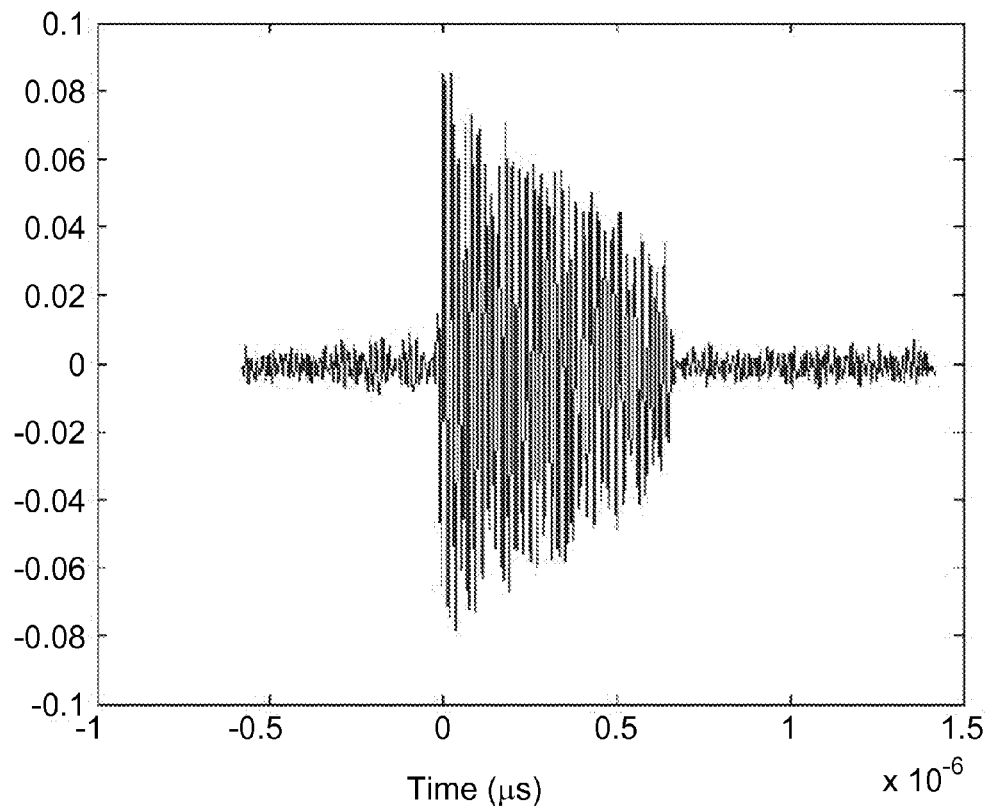
FIG. 13 shows an experimentally measured grating lobe transmit signal when half of the aperture is active and focused off to 25 degrees at f/2. The measurements were obtained using a 64 element 50 MHz phased array with 1.25λ element pitch.

FIGS. 12 and 13 show experimentally measured grating lobe transmit signals when the full 64 element aperture is active and focused off to 25 degrees at f/2 (FIG. 12) and when half of the aperture is active and focused off to 25 degrees at f/2 (FIG. 13). The measurements were obtained using a 64 element 50 MHz phased array with 1.25λ element pitch. A comparison of FIGS. 12 and 13 demonstrates that the length of the grating lobe signal is reduced significantly when only half the aperture is used for transmit.

Figure 14:
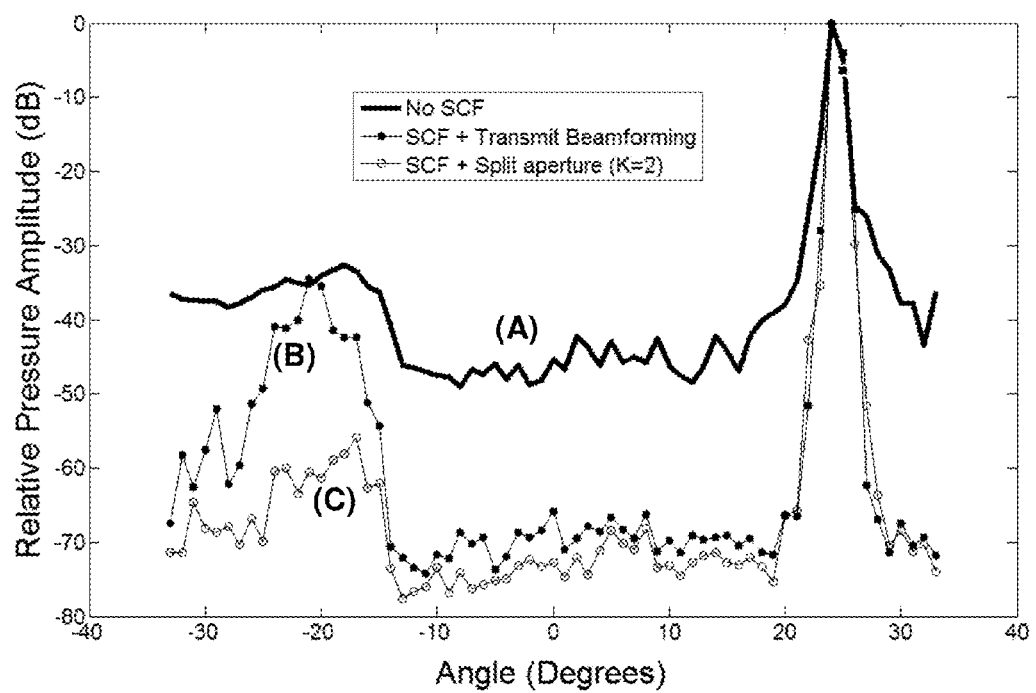
FIG. 14 shows experimentally measured radiation patterns from a 50 micron wire phantom located at 25 degrees and f/2 when the beam is swept from +35 degrees to −35 degrees. Curve (A) shows a radiation pattern measured when no SFC is applied; curve (B) shows a radiation pattern when SCF is applied; and curve (C) radiation pattern when the aperture is split in two (K=2). The measurements were obtained using a 64 element 50 MHz phased array with 1.25, element pitch.

FIG. 14 shows experimentally measured radiation patterns from a 50 micron wire phantom located at 25 degrees and f/2 when the beam is swept from +35 degrees to −35 degrees. Curve (A) shows a radiation pattern measured when no SFC is applied; curve (B) shows a radiation pattern when SCF is applied; and curve (C) shows a radiation pattern when the aperture is split in two (K=2). The measurements were obtained using a 64 element 50 MHz phased array with 1.25 element pitch. As seen in FIG. 14, split-transmit apertures are effective in grating lobe suppression with SCF weighting factors. Specifically, the level of grating lobes in this case are suppressed more than 20 dB when the aperture is split in two. The grating lobe levels could be suppressed even further upon more aperture splits.

Figure 15A:
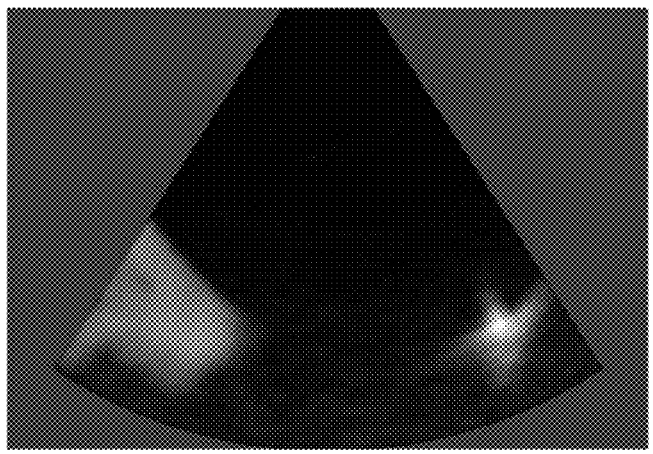
FIG. 15(A) shows an image generated with no SCF processing; (B) an image generated with SCF processing but no aperture splitting on transmit; and (C) an image generated by splitting the transmit aperture in two (K=2) and then applying SCF processing.
Figure 15B:
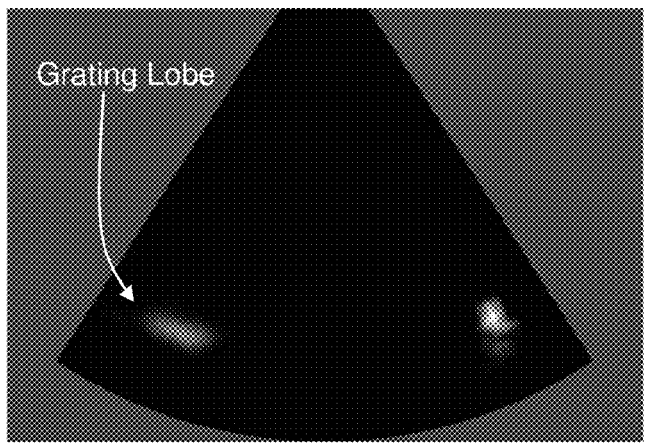
FIG. 15 shows images generated with a 64 element 50 MHz phased array with 1.25, spacing. The image is of a 50-micron wire phantom located at f/2.5. The image depth ranges from 1 mm to 8 mm and the steering angle ranges from +/−35 degrees. All images are displayed with a dynamic range of 60 dB.
Figure 15C:
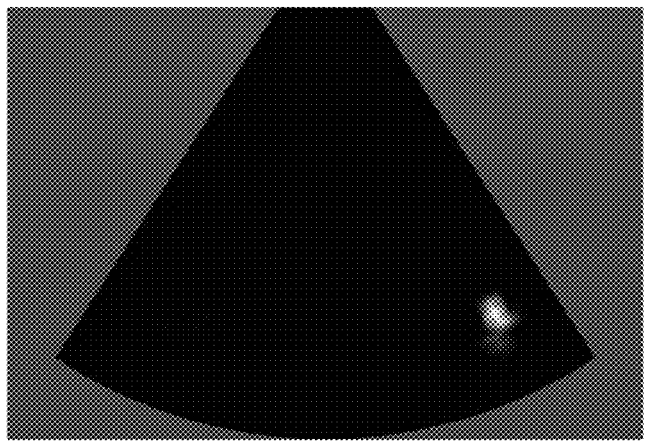

FIG. 15 shows images generated with a 64 element 50 MHz phased array with 1.25λ spacing. The image is of a 50-micron wire phantom located at f/2.5. The image depth ranges from 1 mm to 8 mm and the steering angle ranges from +35 degrees to −35 degrees. All images are displayed with a dynamic range of 60 dB. FIG. 15(A) shows an image generated with no SCF processing; (B) an image generated with SCF processing but no aperture splitting on transmit; and (C) an image generated by splitting the transmit aperture in two (K=2) and then applying SCF processing. As demonstrated by FIG. 15, the use of a split transmit aperture dramatically improves image quality, and when used in conjunction with a processing method such as SCF, results in significant suppression of grating lobes.

Although embodiments of the invention have been described with reference to two-dimensional ultrasound imaging systems, these techniques may be applied in other types of ultrasound imaging systems. For example, in view of this disclosure, one of skill in the art can employ the beamforming and grating lobe suppression techniques in a three-dimensional ultrasound imaging system, without departure from the inventive concepts disclosed herein.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by electrical circuits or equivalent computer programs, microcode, or the like, or any combinations thereof. The described operations and their associated modules may thus be embodied in software, firmware, hardware, or any combinations thereof.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method of ultrasound imaging comprising:
   splitting an array of ultrasound elements into a set of sub-apertures;
   sequentially transmitting a plurality of beamformed pulses along a focused line of sight, such that the beamformed pulses are transmitted from different sub-apertures;
   after each transmit event, receiving echoes with the array of ultrasound elements, thereby obtaining a set of signals associated with each transmit event;
   applying receive beamforming time delays to each set of signals and calculating phase coherence weighting factors for each set of signals;
   employing the phase coherence weighting factors to generate a weighted beamformed signal for each set of signals; and
   adding the weighted beamformed signals to generate a line of an ultrasound image.

2. The method of claim 1, wherein the number of sub-apertures is an integer between 2 and 16.

3. The method of claim 2, wherein the number of sub-apertures is 2.

4. The method of claim 1, wherein the focused ultrasound transmit signal has a frequency greater than 20 MHz.

5. The method of claim 1, wherein the plurality of transmit elements has an element-to-element pitch greater than 0.5 lambda, wherein lambda is the wavelength of the focused ultrasound transmit signal.

6. The method of claim 1, wherein the beamed formed pulses are transmitted at a steering angle greater than 15 degrees.

7. The method of claim 1, wherein beamformed pulses transmitted from at least two of the sub-apertures have an approximately equal length in the time domain in the grating lobe region.

8. The method of claim 1, further comprising: configuring the number of sub-apertures based on a steering angle.

9. The method of claim 1, further comprising: configuring the number of sub-apertures based on a desired signal-to-noise ratio level.

10. The method of claim 1, further comprising repeating the method using different focused lines of sight and generating additional lines of the ultrasound image.

11. The method of claim 1, wherein the sub-apertures have equal widths.

12. A system for ultrasound imaging, the system comprising:
- an imaging array comprising an array of ultrasound elements having an element-to-element pitch greater than 0.5 lambda, wherein lambda is the wavelength of an ultrasound signal;
- a transmit beamformer coupled to the imaging array, wherein the transmit beamformer is configured to sequentially transmit a plurality of beamformed pulses along a focused line of sight, such that the beamformed pulses are transmitted from different sub-apertures of the array of ultrasound elements;
- a receive beamformer coupled to the imaging array, wherein the receive beamformer is configured to receive echoes with the array of ultrasound elements, thereby obtaining a set of signals associated with each transmit event; and
- processing circuitry coupled to the receive beamformer, wherein the processing circuitry is configured to:
- apply receive beamforming time delays to each set of signals and calculate phase coherence weighting factors for each set of signals;
- employ the phase coherence weighting factors to generate a weighted beamformed signal for each set of signals; and
- add the weighted beamformed signals to generate a line of an ultrasound image.

13. The system of claim 12, wherein the number of sub-apertures is an integer between 2 and 16.

14. The system of claim 13, wherein the number of sub-apertures is 2.

15. The system of claim 12, wherein the focused ultrasound transmit signal has a frequency greater than 30 MHz.

16. The system of claim 12, wherein the transmit beamformer is configured to transmit the beamformed pulses at a steering angle greater than 15 degrees.

17. The system of claim 12, wherein the transmit beamformer is configured such that beamformed pulses transmitted from at least two of the sub-apertures have an approximately equal length in the time domain in the grating lobe region.

18. The system of claim 12, wherein the number of sub-apertures is configurable based on a steering angle.

19. The system of claim 12, wherein the number of sub-apertures is configurable based on a desired signal-to-noise ratio level.

20. The system of claim 12, wherein the imaging array comprises a linear shifted aperture ultrasound array.

21. The system of claim 12, wherein the imaging array comprises a phased ultrasound array.

22. The system of claim 12, wherein the system is configured to generate additional lines of the ultrasound image along different focused lines of sight.

23. The system of claim 12, wherein the sub-apertures have equal widths.

* * * * *